US011857359B2

(12) United States Patent
Liu et al.

(10) Patent No.: US 11,857,359 B2
(45) Date of Patent: *Jan. 2, 2024

(54) FAST 3D RADIOGRAPHY WITH MULTIPLE PULSED X-RAY SOURCES BY DEFLECTING TUBE ELECTRON BEAM USING ELECTRO-MAGNETIC FIELD

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AlxScan Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/124,472

(22) Filed: Mar. 21, 2023

(65) Prior Publication Data
US 2023/0255584 A1 Aug. 17, 2023

Related U.S. Application Data

(63) Continuation of application No. 17/412,632, filed on Aug. 26, 2021, now Pat. No. 11,633,168.
(Continued)

(51) Int. Cl.
*A61B 6/00* (2006.01)
*A61B 6/02* (2006.01)
(Continued)

(52) U.S. Cl.
CPC ............. *A61B 6/541* (2013.01); *A61B 6/025* (2013.01); *A61B 6/032* (2013.01); *A61B 6/035* (2013.01); *A61B 6/0407* (2013.01); *A61B 6/06* (2013.01); *A61B 6/08* (2013.01); *A61B 6/405* (2013.01); *A61B 6/4007* (2013.01); *A61B 6/4014* (2013.01); *A61B 6/4021* (2013.01);
(Continued)

(58) Field of Classification Search
CPC ..... A61B 6/4007; A61B 6/4021; A61B 6/025; A61B 6/032
See application file for complete search history.

(56) References Cited

U.S. PATENT DOCUMENTS

2016/0056008 A1\* 2/2016 Mackie .................. H01J 35/13
378/5

\* cited by examiner

*Primary Examiner* — Dani Fox
(74) *Attorney, Agent, or Firm* — PatentPC Power Patent; Bao Tran

(57) ABSTRACT

An X-ray imaging system using multiple pulsed X-ray sources to perform highly efficient and ultrafast 3D radiography is presented. There are multiple pulsed X-ray sources mounted on a structure in motion to form an array of sources. The multiple X-ray sources move simultaneously relative to an object on a pre-defined arc track at a constant speed as a group. Electron beam inside each individual X-ray tube is deflected by magnetic or electrical field to move focal spot a small distance. When focal spot of an X-ray tube beam has a speed that is equal to group speed but with opposite moving direction, the X-ray source and X-ray flat panel detector are activated through an external exposure control unit so that source tube stay momentarily standstill equivalently. 3D scan can cover much wider sweep angle in much shorter time and image analysis can also be done in real-time.

20 Claims, 5 Drawing Sheets

Related U.S. Application Data

(60) Provisional application No. 63/226,508, filed on Jul. 28, 2021, provisional application No. 63/225,194, filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.
| | |
|---|---|
| *G06T 17/00* | (2006.01) |
| *G01N 23/044* | (2018.01) |
| *A61B 6/03* | (2006.01) |
| *A61B 6/06* | (2006.01) |
| *G01N 23/083* | (2018.01) |
| *G01N 23/18* | (2018.01) |
| *G06T 7/00* | (2017.01) |
| *G06T 11/00* | (2006.01) |
| *A61B 6/04* | (2006.01) |
| *G06T 7/11* | (2017.01) |
| *G16H 10/60* | (2018.01) |
| *G16H 30/20* | (2018.01) |
| *G16H 50/20* | (2018.01) |
| *G06V 10/25* | (2022.01) |
| *G06V 10/62* | (2022.01) |
| *A61B 6/08* | (2006.01) |

(52) U.S. Cl.
CPC .......... *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

FAST 3D RADIOGRAPHY WITH MULTIPLE PULSED X-RAY SOURCES BY DEFLECTING TUBE ELECTRON BEAM USING ELECTRO-MAGNETIC FIELD

The present invention claims priority to Provisional Application Ser. No. 63/182,426 filed on Apr. 30, 2021; 63/226,508 filed Jul. 28, 2021; 63/170,288 filed Apr. 2 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

This patent specification is in the field of 3D X-ray radiography systems and methods and particularly to using pulsed X-ray sources and X-ray digital flat panel detector.

BACKGROUND

Digital Tomosynthesis (DIS) performs high-resolution limited-angle tomography at radiation dose levels comparable with conventional radiography.

When tomosynthesis is performed, the X-ray source would need to move in an arc around a scanned object. While the X-ray source moves around the object, a series of X-ray images are acquired at different angles.

The collected data set permits the reconstruction of parallel planes. Each plane is in focus, and those that are out-of-plane tissue images are blurred. Usually, a wider sweep angle would generate more data projections and result in better 3D resolution, but it takes longer. In addition, data processing is manufacturer-specific because different reconstruction algorithms might be used.

These kinds of digital tomosynthesis systems and methods can be applied to X-ray 3D radiography applications such as X-ray mammography, X-ray 3D chest diagnosis system for COVID, X-ray 3D Non-Destructive Test (NDT) system, and X-ray 3D security inspection system.

There are prior arts with the single X-ray source and single flat panel to perform X-ray 3D radiography. However, there are disadvantages among prior arts.

The main disadvantage is that a single X-ray source takes a very long time to acquire good data projections. It is true for both continuous mode and step-and-shoot mode. In continuous mode, the X-ray source emits X-ray while it is moving; in step-and-shoot mode, the X-ray source moves to a location, stops and emits X-ray, and continues moving to the next location.

Although all patients hope X-ray imaging could be done as fast as possible, there is a minimum X-ray source travel sweep angle requirement. If the sweep angle is too small so that the X-ray source can travel less and the total time needed is less, then the system will have smaller numbers of data projections. The smaller number of data projections would result in lower depth resolution and loss of details perception. On the other hand, if the sweep angle needs to be large enough for good data projections for better 3D resolution, then a single X-ray source may mechanically travel too long that patients will feel uncomfortable and cannot hold breast standstill anymore. In some cases, a 50-degree sweep would take as long as about half a minute.

The second disadvantage is that it is difficult to do real-time reconstruction because the whole thing is slow. Usually, prior art takes tens of seconds to finish sweeping.

A Fast 3D Radiography with multiple pulsed X-ray sources by deflecting X-ray tube electron beam using either electrical field or magnetic field is proposed in the current invention. It utilizes motion control, multiple pulsed X-ray sources, and deflecting electrical field or magnetic field.

The mechanism of deflecting electron beam by the magnetic field is similar to using magnetic deflection yoke at cathode ray tubes. However, this invention is to deflect the electron beam only horizontally in one direction.

Another way of deflecting an electron beam is to put one pair of electrodes inside or outside the X-ray tube after the electron gun structure. Electrostatic deflection is more common for high frequencies than driving the large inductance of a deflection magnetic yoke.

Compared with electrostatic deflection, magnetic deflection has fewer obstructions at the X-ray tube, allowing for a larger-diameter electron beam.

SUMMARY

In a first aspect, a system to provide fast 3D radiography using multiple pulsed X-ray sources in motion with a primary motor stage moving freely on an arc rail with a predetermined shape; a primary motor that engages with said primary motor stage and controls a speed of the primary motor stage; a plurality of X-ray sources each moved on the primary motor stage; a supporting frame structure that provides housing for the primary motor stage; a flat panel detector to receive X-ray imaging data; a deflection plate to produce electrical field or a magnetic coil yoke to produce a magnetic field at X-ray tube electron beam.

In a second aspect, a method of fast 3D radiography using multiple pulsed X-ray sources in motion includes positioning a primary motor stage to a predetermined initial location; sweeping the primary motor stage at a predetermined constant speed by said primary motor; deflecting X-ray tube electron beam with a predetermined sequence by applying a voltage to plate or by applying current to magnetic coil; electrically activating an X-ray source and an X-ray flat panel detector when an X-ray tube focal spot moves in the opposite direction to that of the primary motor stage and at a selected speed of the primary motor stage; and acquiring image data from the X-ray source with a flat panel.

In another aspect, an X-ray imaging system using multiple pulsed X-ray sources in motion to perform ultrafast, highly efficient 3D radiography is presented. In the system, multiple pulsed X-ray sources are mounted on a structure in motion to form an array of the source. The multiple X-ray sources move simultaneously around an object on a pre-defined track at a constant speed of a group. X-ray tube focal spot at each X-ray source can also move rapidly around its static position of a small distance by deflection electrical field or deflection magnetic field. When an X-ray tube focal spot on an individual X-ray source has a speed equal to group speed but an opposite moving direction, the individual X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. X-ray receptor is an X-ray flat panel detector. 3D radiography image projection data can be acquired with an overall much wider sweep in a much shorter time period, and image analysis can also be done in real-time while the scan goes.

In another aspect, an X-ray imaging system using multiple pulsed X-ray sources in motion to perform highly efficient and ultrafast 3D radiography includes multiple pulsed X-ray sources mounted on a structure in motion to form an array of sources. The multiple X-ray sources move simultaneously relative to an object on a pre-defined arc track at a constant speed as a group. Focal spot at each individual X-ray source can also move rapidly around its static position at a small distance. When X-ray tube focal spot of an individual X-ray source has a speed that is equal to group speed, but with opposite moving direction, the individual X-ray source and X-ray detector are activated through an external exposure control unit. This arrangement allows the X-ray source to stay relatively standstill during the X-ray source activation and X-ray detector exposure, X-ray receptor is an X-ray flat panel detector. Multiple X-ray source in motion operation results in a much-reduced source tube travel distance for individual X-ray sources. 3D radiography image data can be acquired with an overall much wider sweep angle in a much shorter time, and image analysis can also be done in real-time while the scan goes.

In implementations, the X-ray can also be randomly activated from one of any sources in the array using a random-firing scheme. Results of each and accumulated analysis determines the next X-ray source and exposure condition. 3D X-ray radiography images are reconstructed based on each image with an angled geometry of X-ray exposure source. Much broader applications include 3D mammography or Tomosynthesis, chest 3D radiography for COVID or fast 3D NDT, fast 3D X-ray security inspection.

Advantages of the above systems may include one or more of the following. The various embodiment of multiple X-ray sources in motion is used in a novel ultrafast 3D radiography system.

The first advantage is that system overall is several times faster. Each X-ray source would only need to mechanically travel a small fraction of the whole distance in an arc trajectory. It greatly reduces the amount of data acquisition time that is needed fora patient at the X-ray diagnosis machine.

The second advantage is that image analysis can also be done in real-time as the scan goes. Judgment on the images taken will have an impact on the X-ray source focal spot position for the next shot. There is no need to wait until the finish of the whole image acquisition to do layered image reconstruction.

The third advantage is that acquisition of high resolution, and high contrast images are possible due to reduction of motion artifacts. Each X-ray source has its electrical field or magnetic field that can move the X-ray source focal spot around its origin. The composition of focal spot moving speed and track speed leads to the relative standstill position of the X-ray sources at the moment the individual X-ray source is activated.

The fourth advantage is that system can go a much wider sweep to acquire more data projections while being faster. More data projections mean better image construction that would lead to a reduced misdiagnosis rate.

The fifth advantage is that because of a wider angle and faster imaging acquisition, and it is possible to add time components to 3D spatial imaging to form 4D imaging data set.

The present invention has been described in terms of the preferred embodiment, and it is recognized that equivalents, alternatives, and modifications, aside from those expressly stated, are possible and within the scope of the appending claims.

DETAILED DESCRIPTION

The following discussion describes in detail one embodiment of the invention (and several variations of that embodiment). However, this discussion should not be construed as limiting the invention to those particular embodiments. Practitioners skilled in the art will recognize numerous other embodiments as well. For definition of the complete scope of the invention, the reader is directed to appended claims.

Thus, for example, it will be appreciated by those of ordinary skill in the art that the diagrams, schematics, illustrations, and such as represent conceptual views or processes illustrating systems and methods embodying this invention. The functions of the various elements shown in the figures may be provided through the use of dedicated hardware and hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and operating systems described herein are for illustrative purposes and, thus, are not intended to be limited to any particular named manufacturer.

Figure 1:
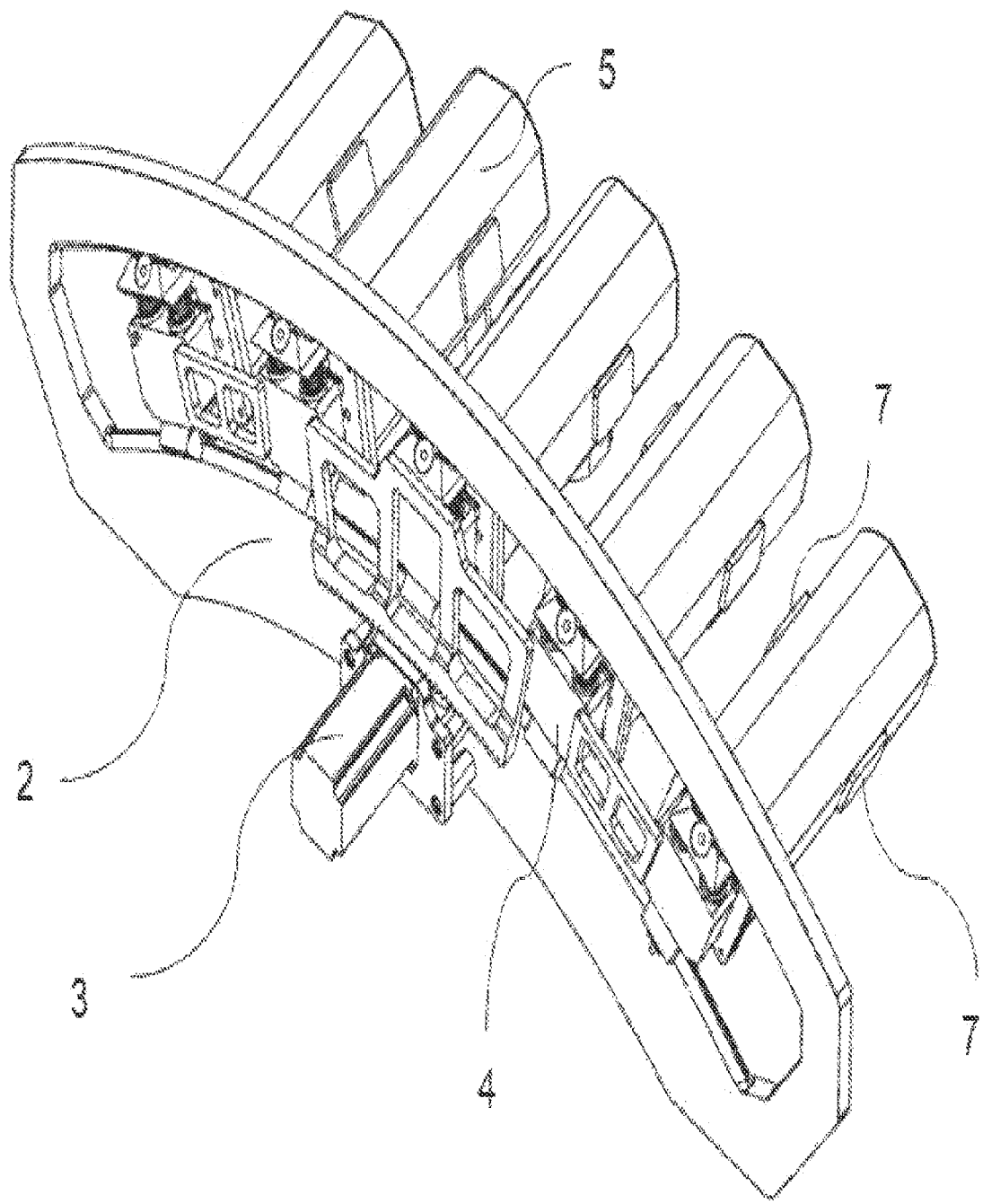
FIG. 1 illustrates an ultrafast 3D digital radiography system with multiple X-ray source tubes in motion using deflection electrical field.

A novel ultrafast 3D digital imaging system with multi pulsed X-ray sources by deflecting tube electron beam using electrical field is shown in FIG. 1. It comprises a primary motor 3 engaged with a primary motor stage 4, multiple X-ray tubes 6, each in X-ray source tube housing 5 and a pair of deflection electrical plates 7 on each side of each tube 6. The X-ray source tube housings 5 are mounted on a supporting frame structure 2, all of which move together on the primary motor stage 4.

Figure 4:
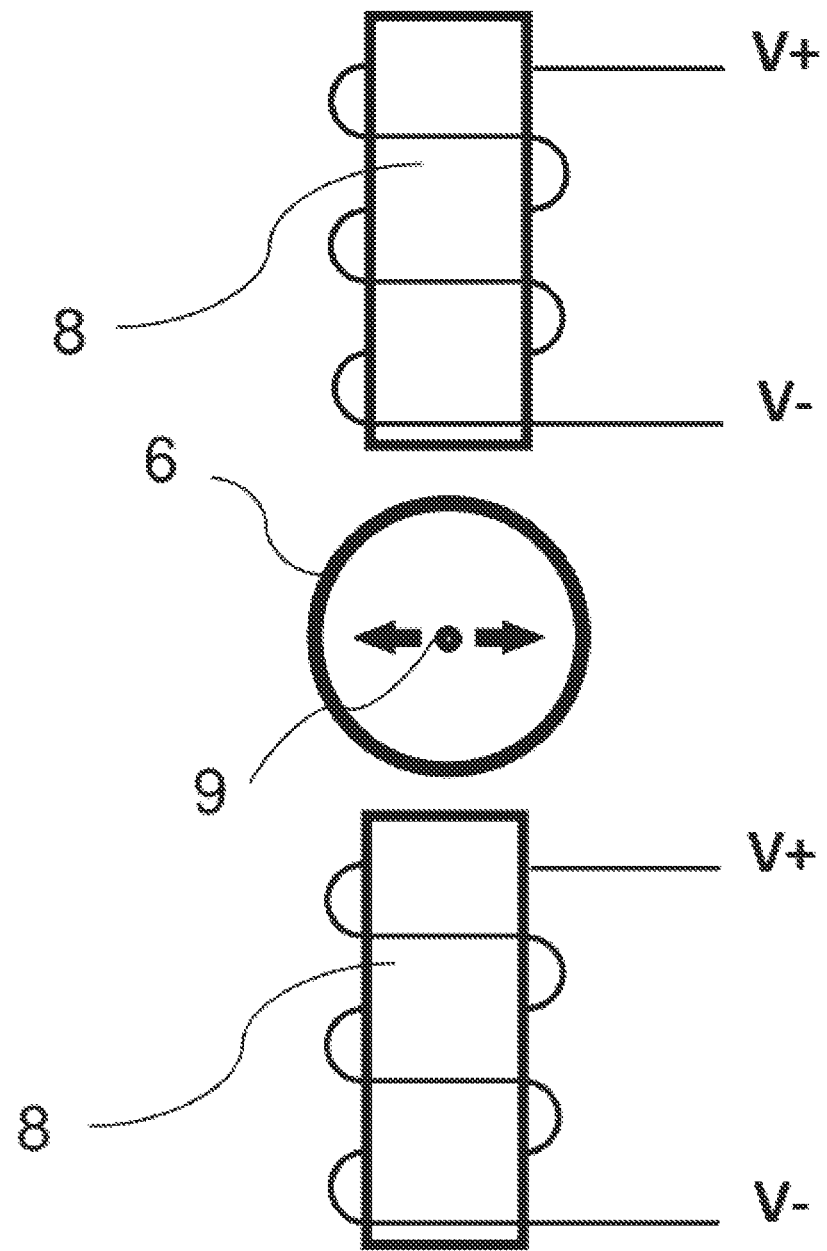
FIG. 4 illustrates an exemplary deflection of electron beam in an X-ray tube by a pair of magnetic coils when current flows through the coils.
Figure 5:
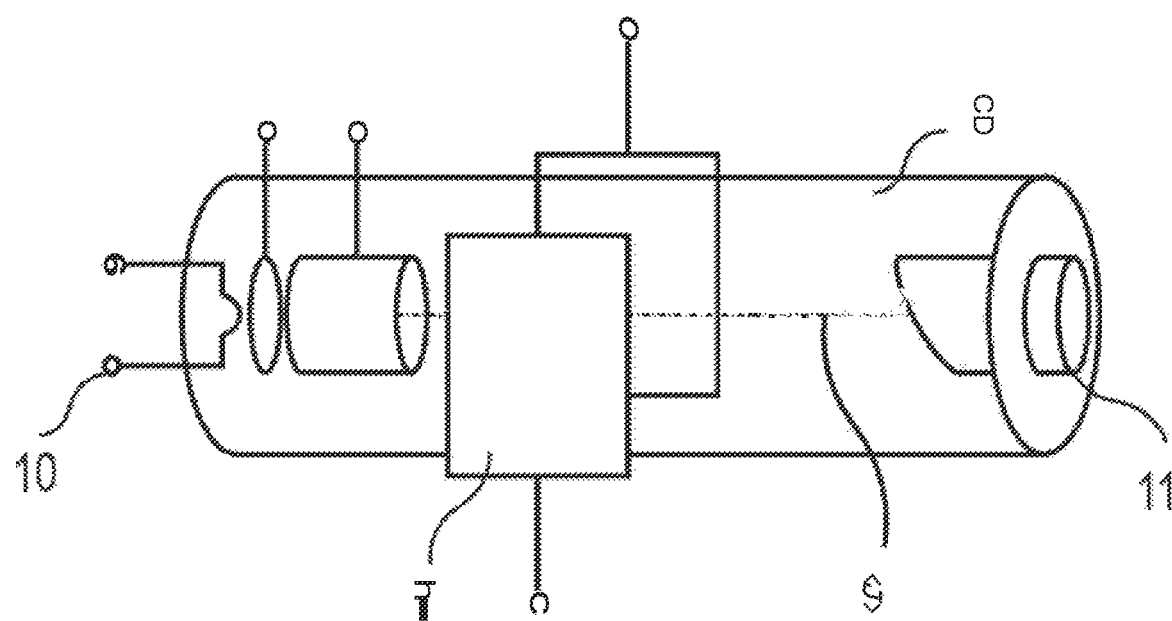
FIG. 5 illustrates an exemplary deflection of electron beam in an X-ray tube by a pair of electric plates through a voltage difference.

By applying a voltage difference at the electrical deflection plate 7, an electrical field will be created between the electrical deflection plates 7 as shown in FIG. 5. The strength of the electrical field varies upon the voltage applied. The deflection of the electron beam of the X-ray tube can be achieved by using a deflection magnetic field as shown in FIG. 4. A primary motor 3 mechanically engages with a primary motor stage 4 to control the speed of the primary motor stage 4. X-ray sources move in arcs at the same speed as the primary motor stage 4, with the primary motor 3 being on one side of the primary motor stage 4. A supporting frame structure 2 provides housing for the primary motor stage 4 and X-ray sources. A flat panel detector 1 receives X-ray imaging data. A pair of deflection plates 7 or a pair of magnetic coils 8 yoke produces an electrical field or a magnetic field at the X-ray tube electron beam 9.

The multiple pulsed X-ray sources or X-ray tubes 6 are mounted on the primary motor stage 4 to form an array of sources. The multiple X-ray sources move simultaneously relative to an object on a pre-defined arc track at a constant speed as a group. Electron beam 9 inside each individual X-ray tube can be deflected by magnetic or electrical field to move focal spot a small distance. When the focal spot of an X-ray tube beam has a speed that is equal to group speed but with opposite moving direction, the X-ray tube 6 and X-ray flat panel detector 1 are activated through an external exposure control unit so that source tube stay momentarily standstill equivalently. With the multiple sources or X-ray tubes 6 working parallel, the system only moves a fraction of the distance that a single tube system has to move. As a result, the 3D scan can cover much wider sweep angle in much shorter time and image analysis can also be done in real-time.

To power the structure in motion, the primary motor 3 engages primary motor stage 4 by gears. Primary motor 3 can move primary motor stage 4 along a rigid rail at a predetermined constant speed. By applying a voltage to a pair of deflection electrical plates 7 at X-ray tube 6, the electron can be deflected before X-ray tube electrons reach the X-ray tube target 11. By fine-tuning voltage, the electron focal spot can move along the direction of primary motion stage 4. When focal spot speed is equal to the primary motion stage 4 and has an opposite direction, then X-ray tube 6 and X-ray flat panel detector 1 are triggered. At this trigger moment, X-ray tube 6 and X-ray detector 1 actually have a relative standstill position.

The primary motion stage 4 with the X-ray source(s) is moved on an arc rail with a predetermined shape, and the X-ray source(s) is moved on said primary motion stage 4 at a constant speed by said primary motor 3. Multiple X-ray sources are mounted on said primary motion stage 4 in the form of an array of sources. The multiple X-ray sources move simultaneously around an object on a pre-defined track at a constant speed as a group. The focal spot of the X-ray source can also move rapidly around its static position of a small distance. When an X-ray tube focal spot on an individual X-ray source has a speed equal to group speed but an opposite moving direction, the respective X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. A flat panel detector 1 is placed on a supporting frame structure to receive X-ray imaging data. A pair of deflection plate 7 or a magnetic coil 8 yoke is positioned to produce an electrical field or a magnetic coil at an X-ray tube electron beam 9.

Multiple X-ray tubes 6 in an array and the detector will be mechanically moved in a predetermined arc track by a primary motor stage 4. A set of multiple X-ray tubes can be connected to a primary motor stage 4 via a rack and pinion type mechanical structure or fixed on a plurality of bases with a fixed distance between each other. The X-ray tube focal spot is deflected in one direction and opposite direction by electric field or magnetic field. While moving on the arc track, individual X-ray tubes would move rapidly around their static position by a deflecting electric field or magnetic field. X-ray sources from one of the sources can be randomly activated through the control unit, in which 3D radiography image data acquisition and image analysis can be made in real-time while the scan goes. A preferred method to trigger multiple pulsed X-ray sources in motion includes positioning a primary motor stage 4 to a predetermined initial location; sweeping the primary motor stage at a predetermined constant speed by said primary motor 3; deflecting X-ray tube electron beam 9 with a predetermined sequence by applying a voltage to plate or by applying current to magnetic coil; electrically activating an X-ray source and a flat panel detector 1 when an X-ray tube focal spot moves in an opposite direction to that of the primary motor stage 4 and at a selected speed of the primary motor stage 4; and acquiring image data from an X-ray flat panel detector 1.

X-ray source tube housing 5 is pivotally mounted on an axis parallel to the X-ray source mounting plate and coupled to a rotation driving mechanism that causes the X-ray source tube housing to rotate around an axis parallel to the X-ray source mounting plate. The angle of rotation is designated by an angle "β" in this application. The amount of angle of rotation can be set by the user based on specific requirements. In an exemplary embodiment, the angle of rotation is about 12.5 degrees. A single rotation driver couples the X-ray source tube housing 5 to a geared motor for rotating X-ray source tube housing 5. The rotation driving mechanism comprises two pairs of pulleys and, wherein each pair of pulleys is mounted on each end of X-ray source tube housing 5 and is coupled by drive gears. They drive gears and rotate X-ray source tube housing 5 when the rotation driver is activated by software. A preferred speed range of the X-ray tube housing 5 is from about 20 mm/s to about 50 mm/s.

A pair of deflection electrical plates 7 is disposed to an arc of the X-ray source and an X-ray flat panel detector 1. The deflection electrical plates 7 are adjusted to a position where the X-ray source and the flat panel detector 1 are not in line. When the arcuate shape is pre-defined, and the X-ray source is mechanically moved in a circular motion around its focal point in accordance with a speed control unit that controls the speed of the primary motor 3 in conjunction with the X-ray exposure control unit that controls the time duration of the X-ray output from the X-ray source through trigger signal generated from trigger source, the X-ray source will trace out a curve in 3D space on the detector. At the same time, the X-ray source will also race out a corresponding curve on the detector with some degree rotation in 3D space. Image data can be reconstructed with knowledge of the target object structure at each location that the X-ray source moves through. Knowledge of the target object geometry can be calculated with pre-measured landmarks and image processing tools to yield accurate geometric modeling of the interior body structures within the patient. One embodiment includes a two-dimensional or set of 3D cameras to detect patient movement during the procedure and compensate for the patient movement in real-time.

A supporting frame structure 2 provides housing for the X-ray source moving mechanism. An arc rail, which can be part of a single axis motion stage, is provided to move along a circular track in one direction. An electronic controller (not shown) allows the speed of the arc rail to be precisely controlled. A plurality of pulsed X-ray sources is mounted on the moving mechanism in an array around the periphery of the arc rail. For the X-ray sources, any suitable type of X-ray tube may be used. The arc rail and its related structure can be moved smoothly on the supporting frame structure 2 at high speed and minimal friction. Each X-ray source is triggered when it comes into position relative to a patient during a sweep. Each X-ray source must be positioned so that the focal spot of the X-ray source does not irradiate any portion of the patient until the X-ray source is triggered.

In one embodiment, the system uses multiple pulsed X-ray sources in motion to perform ultrafast, highly efficient 3D radiography. In the system, multiple pulsed X-ray sources are mounted on a structure in motion to form an array of the source. The multiple X-ray sources move simultaneously around an object on a pre-defined track at a constant speed of a group. X-ray tube focal spot at each X-ray source can also move rapidly around its static position of a small distance by deflection electrical field or deflection magnetic field. When an X-ray tube focal spot on an individual X-ray source has a speed equal to group speed but an opposite moving direction, the respective X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. X-ray receptor is an X-ray flat panel detector 1. As a result, 3D radiography image projection data can be acquired with an overall much broader sweep in a much shorter time, and image analysis can also be done in real-time while the scan goes.

Figure 2:
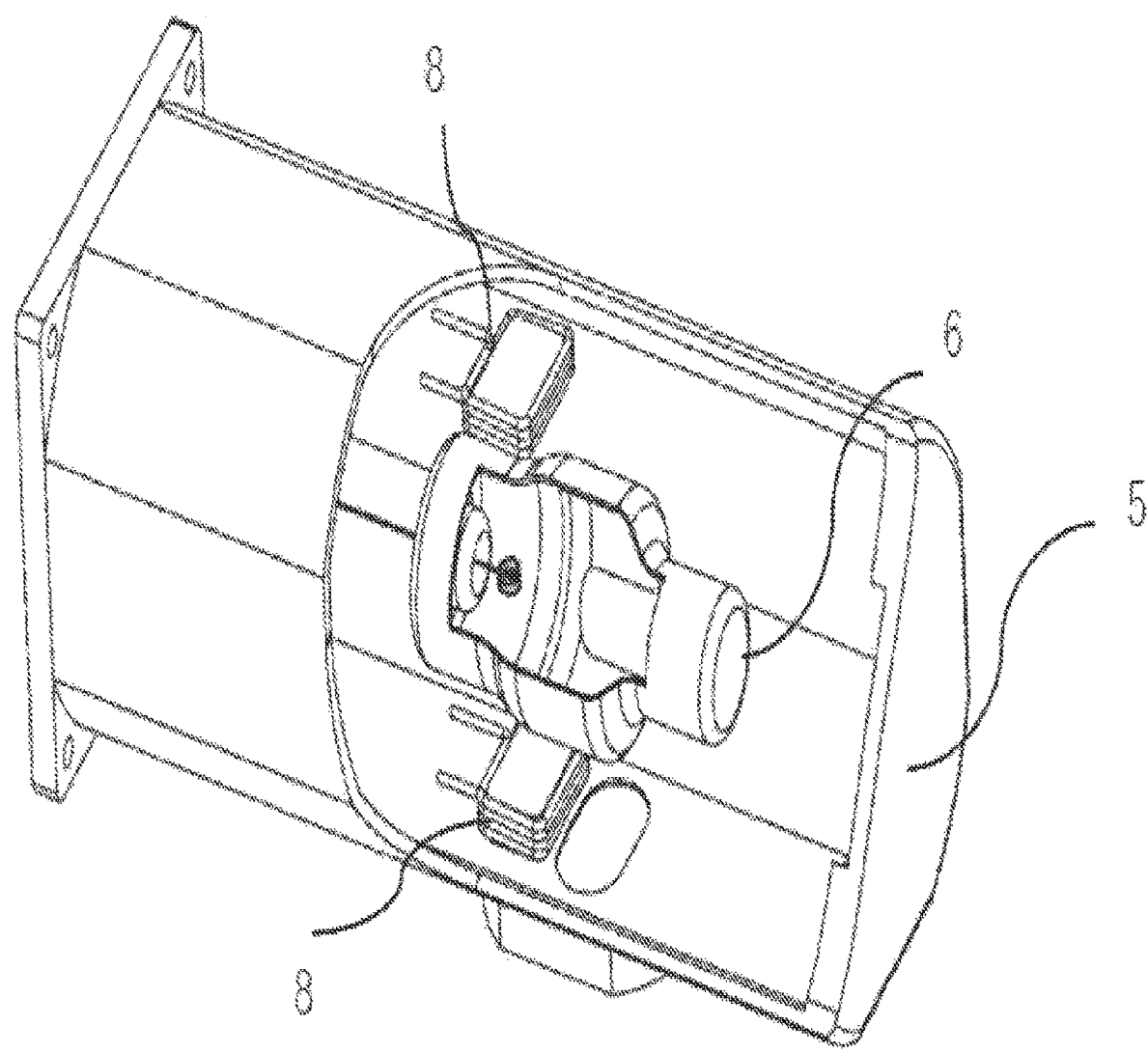
FIG. 2 illustrates part of an ultrafast 3D digital radiography system with X-ray source tube in motion using deflection magnetic field.

More details of the ultrafast 3D digital imaging system with multi pulsed X-ray sources by deflecting tube electron beam 9 using deflection magnetic field is shown in FIG. 2, which shows one of the multiple X-ray sources, each of which includes a pair of magnetic deflection coil 8 are placed at an X-ray tube 6 inside an X-ray source tube housing 5. By applying current at the magnetic deflection coil 8, a magnetic field will be created between the pair of the magnetic deflection coil 8. The strength of the magnetic field varies upon the current flow through the magnetic coil.

During operation, primary motor 3 engages primary stage 4 by gears to provide motion for the X-ray sources in the housings 5. Primary motor 3 can move primary stage 4 along the rigid rail at a predetermined constant speed. By applying current to a pair of magnetic deflection coils 8 at X-ray tube 6, X-ray tube electron beam 9 can be deflected by force from the magnetic field before the electrons reach the X-ray tube target. By fine-tuning the current, the electron focal spot can move along the direction of primary motor stage 4. When X-ray tube focal moving speed is equal to the speed of primary motion stage 4 and has an opposite direction, then X-ray tube 6 and X-ray detector 1 are triggered. At this trigger moment, X-ray tube 6 and X-ray detector 1 actually have a relative standstill position.

The X-ray tube 6 is the heart of the X-ray machine. The X-ray tube 6 has high voltage terminals connected to an external high voltage power supply through electrical wires. The X-ray tube 6 produces a current flow along an electron gun column in a vacuum container inside the X-ray tube 6.

A pair of magnetic deflection coils 8 is used to adjust the beams of the X-ray tube 6. The X-ray tube 6 or source could be a point source, smaller focal spot size is desirable. Smaller focal spot size would have better image resolution. A spectrally filtered X-ray tube is desirable to produce an X-ray beam of desired energy range. A tube-mount assembly provides an electrical and mechanical connection between the X-ray tube 6 and the primary motor stage 4. Tube-mount assembly has a secondary or tertiary or more level of metal to shield against electrical interference. A front and back cover and respectively could provide shielding against ambient radiation and airborne particles.

The X-ray source tube housing 5 with an X-ray tube 6 mounted inside is moveable on the primary motor stage 4. The X-ray source tube housing 5 is mounted at primary motor stage 4 that moves freely on an arc rail at a predetermined constant speed; a primary motor 3 that controls a speed of the primary motor stage 4; and multiple X-ray sources (one of which is) housed in the X-ray source tube housing 5 that is all moved simultaneously at the same speed as the primary motor stage 4. An X-ray flat panel detector 1 is to receive X-ray and send imaging data. It is mounted around the rotation center of the primary motor stage 4 to receive the X-ray beam transmitted through a portion of the object under test placed at the rotation center. An array of five X-ray sources is mounted on the X-ray source tube housing 5 at an equal angle to each other; they move together with the primary motor stage 4 at a constant speed. A collimator positioned between the X-ray source tube housing 5 and the flat panel X-ray detector 1 along the axis of motion of the primary motor stage 4 can limit the horizontal component of the X-ray beam passing through. A supporting frame structure 2 provides housing for the primary motor stage 4 and an electrical field deflection device such as a pair of deflection plates 7.

Primary motor 3 provides driving motion to move the primary motor stage 4 on a predetermined track. A plurality of X-ray sources is mounted on the primary motor stage 4 for emitting X-rays sequentially. The X-ray sources are arranged in an array configuration, each X-ray source moving simultaneously with the others on the primary motor stage along the same path, at a constant speed and speed as a group. A flat panel detector 1 is usually mounted on the supporting frame structure 2 to receive X-ray and send imaging data. A pair of electrical deflection plates 7 or magnetic deflection coil 8 yoke is located in front of the X-ray tube target 11 to control the position of the X-ray source focal spot. Technical features of an X-ray imaging system using multiple pulsed X-ray sources in motion to perform ultrafast, highly efficient 3D radiography: The first technical feature is that the primary motor stage 4 is moved on a predetermined track. Each X-ray source is moved with the primary motor stage 4 on the predetermined track, the X-ray sources moving simultaneously with the others on the primary motor stage 4 along the same path, at a constant speed and speed as a group.

Primary motor stage 4 may be moved freely on an arc rail with a predetermined shape. A primary motor 3 that engages with the primary motor stage 4 controls the speed of the primary motor stage 4. In certain implementations, X-ray sources may be mounted on the primary motor stage 4 and move simultaneously around an object on a pre-defined track at a constant speed of a group. X-ray tube focal spot at each X-ray source can also move rapidly around its static position of a small distance by deflection electrical field or deflection magnetic field. When an X-ray tube focal spot on an individual X-ray source has a speed equal to group speed but an opposite moving direction, the respective X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. X-ray receptor is an X-ray flat panel detector 1. As a result, 3D radiography image projection data can be acquired with an overall much broader sweep in a much shorter time, and image analysis can also be done in real-time while the scan goes.

Primary motion stage 4 is mounted on the fixed base structure of a frame and is placed so that it can move freely on an arc rail with a predetermined shape. A primary motor 3 drives the primary motor stage 4. The primary motor speed controller controls the speed of the primary motor stage based on desired movement time and input from the computer system (or programmed timing) during a scan. A power supply is connected to the primary motor to provide electricity for primary motor operation. The primary motor stage 4 is a drive element that moves in a sweeping motion along the rail of the base structure in the direction at a constant speed, controlled by the primary motor 3. The center of the primary motor stage 4 is a cylinder supporting an X-ray tube and a high voltage generator.

X-ray flat panel detector 1 of an X-ray imaging system to provide fast 3D radiography using multiple pulsed X-ray sources in motion with a primary motor stage 4 moving freely on an arc rail with a predetermined shape; a primary motor 3 that engages with said primary motor stage 4 and controls a speed of the primary motor stage 4; a plurality of X-ray sources each moved on the primary motor stage 4; a supporting frame structure 2 that provides housing for the primary motor stage 4; a flat panel detector 1 to receive X-ray imaging data; a pair of deflection plates 7 to produce electrical field or a pair of magnetic coil 8 yoke to produce a magnetic field at X-ray tube electron beam 9. A method of fast 3D radiography using multiple pulsed X-ray sources in motion includes positioning a primary motor stage 4 to a predetermined initial location; sweeping the primary motor stage at a predetermined constant speed by said primary motor 3; deflecting X-ray tube electron beam 9 with a predetermined sequence by applying a voltage to plate or by applying current to magnetic coil 8; electrically activating an X-ray source and a flat panel detector when an X-ray tube focal spot moves in an opposite direction to that of the primary motor stage 4 and at a selected speed of the primary motor stage 4; and acquiring image data from a flat panel detector. In one embodiment, an X-ray imaging system using multiple pulsed X-ray sources in motion to perform ultrafast, highly efficient D radiography is presented.

Figure 3:
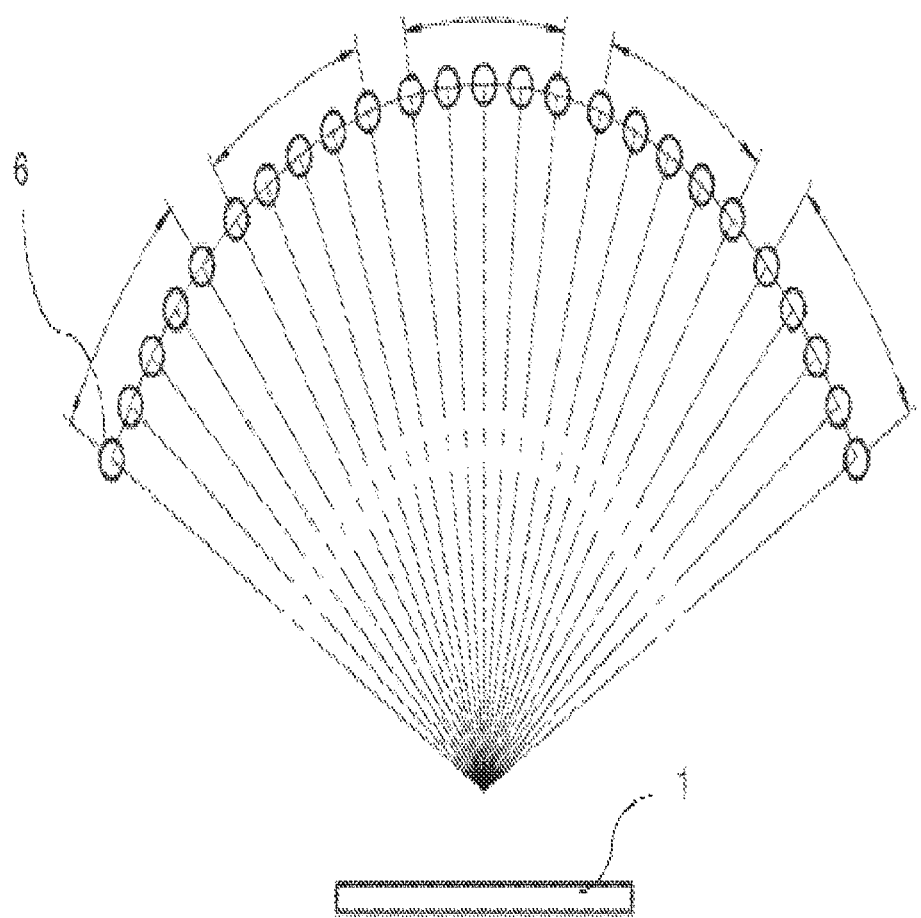
FIG. 3 illustrates that a five-X-ray-source system that takes 25 sets of projection data by each X-ray source traveling only one-fifth of the total distance.

FIG. 3 illustrates an exemplary complete X-ray exposure position. In this example, there are there are five X-ray tubes 6 in X-ray source tube housing 5, and the five X-ray tubes 6 at X-ray source tube housing 5 perform 25 total X-ray exposures at different angle positions. Each of the five X-ray tubes 6 only needs to travel one-fifth of total covered angle. Therefore, with multiple X-ray tubes 6 working in parallel, a large amount of projection data can be acquired in a fraction of amount of time compared with that of a single X-ray source. An X-ray flat panel detector 1 is served as an X-ray receiver. Electronic signal always goes faster than that of mechanical motion, bottle neck of limiting factor is always motor stage motion itself. Next bottleneck is detector readout limitation. Because detector also needs some time to read out many Mega pixel data and then transfer to a computer.

In view of the widely available superfast computer available, image analysis can be done in real-time with the image acquisition. Judgment on the images taken will have an impact on the X-ray tube 6 position for the next shot. There is no need to wait until finish of whole image acquisition to do image reconstruction. FIG. 3 illustrates that a five-X-ray-source system takes 25 sets of projection data by traveling only one-fifth of the total distance. X-ray tubes 6 are a group of multiple pulsed X-ray sources to form an array of sources or multiple groups of pulsed X-ray sources mounted on a structure in motion to form an array of sources. The multiple X-ray sources move simultaneously relative to an object on a pre-defined arc track at a constant speed as a group. A focal spot at each X-ray source can also move rapidly around its static position at a small distance. When the X-ray tube focal spot of a respective X-ray source has a speed equal to group speed but an opposite moving direction, the X-ray source and an X-ray detector are activated through an external exposure control unit.

This arrangement allows the X-ray source to stay relatively standstill during the X-ray source activation and X-ray detector exposure. X-ray receptor is an X-ray flat panel detector. The first advantage is that system overall is several times faster. Each x-ray source would only need to mechanically travel a small fraction of the whole distance in an arc trajectory. It greatly reduces the amount of data acquisition time needed for a patient at the X-ray diagnosis machine. The second advantage is that image analysis can also be done in real-time as the scan goes. Judgment on the images taken will impact the X-ray source focal spot position for the next shot.

X-ray source tube housing 5 contains a primary X-ray tube 6 powered by a high voltage generator. In this patent, only one primary X-ray tube source is described, but it should be understood that more than one source may be used at the same time to acquire different parts of a 3D image data set. Primary X-ray tube housing 5 is mounted on a moveable structure (not shown) with a motor control system to enable movement in any direction on an arc rail that forms a part of a circular arc track or helical motion track around the patient. The high voltage generator outputs a high voltage electrical current that flows through power cables that go to the input connectors on the backside of the primary X-ray tube. In addition, the X-ray source can have a separate voltage controller that can adjust the output voltage for both high voltage primary X-ray tube and individual X-ray tube focal spot moving voltage to control the focal spot position around the static position.

Multiple X-ray tubes 6 are arranged in an array. The X-ray tubes 6 are mounted on a structure moved relative to the object by a primary motor on an arc rail in the exemplary embodiment. A sequence of moving the structure of the X-ray tubes at a constant speed and a slight angle is pre-defined to generate an array of the X-ray tubes in motion simultaneously around the object. At each time point, the direction of the movement of the X-ray tube, the distance between adjacent X-ray tubes, and the time delay between adjacent X-ray tubes can be determined to form an arc trajectory for all the X-ray tubes. At a certain timing point, each X-ray tube's focal spot (electron beam) is moved around its static position by a predetermined electrical field or magnetic field from a deflection plate. A high voltage supply can produce a deflection electrical field at a pair of deflection plates that deflects the focal spot of the X-ray tube from its static position by a predetermined distance to a new location that forms a predetermined geometric shape as illustrated in FIG. 5.

X-ray flat panel detector 1 is used as a detector of an X-ray imaging system. X-ray flat panel detector 1 comprises a plurality of individual detector panels arranged in two dimensions to form a square or rectangular shape and can be sensitive to X-rays. The X-ray flat panel detector 1 is an ultra-high speed, high efficiency, active pixel sensor flat panel detector 1 with a fast readout capability. X-ray flat panel detector 1 can provide images at frame rates higher than 25 fps. X-ray flat panel detector 1 includes each detector panel that can be individually addressed for readout by address unit through panel driver. The X-ray tube 6 is located inside the X-ray machine with the X-ray tube focal spot moved by deflection electrical field or deflection magnetic field from the X-ray controller. X-ray controller triggers X-ray tube 6 activation bypassing trigger signal to the X-ray power supply.

A pair of magnetic deflection coils 8 are positioned near the X-ray tube in FIG. 4. X-ray sources have a focal spot that can move by the magnetic field generated by coils and, respectively.

FIG. 4 illustrates an exemplary deflection of an electron beam in an X-ray tube can be deflected by magnetic coils 8 when current flows through the coils. X-ray tube 6 can be fixed on a supporting frame or have an electrically actuated mechanism to enable X-ray focal spot positioning. In the latter case, the X-ray tube can move with a primary motor stage 4 with the primary motor engaged to rotate a rotor shaft, thus controlling the speed of the primary motor stage 4. On the other hand, a deflection plate is mounted to a platform at an equal distance from X-ray sources. The plate is part of a voltage/current drive system that can generate an electrical field or magnetic field. The plate is driven by a control board that receives commands from the exposure control unit via a digital interface. The voltage from the exposure control unit passes through a converter to energize the electrical coils of the magnetic coil, which generates a magnetic field surrounding the X-ray tube. An exposure control unit controls a magnetic coil through a magnetic coil driver. After starting a scan sequence, the control board triggers individual pulsed X-ray sources through a signal cable with digital signals generated by the exposure control unit. Upon receiving a trigger command, respective pulsed X-ray sources begin a ramp-up operation to increase power output.

In an embodiment, the X-ray source in the X-ray tube is stationary at the beginning of the operation, but when it is time to expose the X-ray receptor (flat panel detector), it moves in an opposite direction from the primary motor stage 4 while being fired with a selected speed. In another embodiment, the X-ray source can be turned on randomly by triggering either from outside the system or from inside the system using a random firing scheme. Results of each and accumulated analysis determine the next X-ray source and exposure condition. 3D X-ray radiography images are reconstructed based on each image with an angled geometry of the X-ray exposure source. Much broader applications include 3D mammography or tomosynthesis, chest 3D radiography for COVID or fast 3D IDT, fast 3D X-ray security inspection.

X-ray tube electron beam 9 and flat-panel detector 1 are positioned in a parallel arrangement to each other. X-ray tube focal spot moves around the static position at a small distance on X-ray tube anode due to magnetic field produced by magnetic coil yoke or electrical field produced by deflector plates, depending on its design. At each instance of X-ray tube focal spot's movement around its origin, the x-ray beam projected onto a region of interest is determined by x-ray tube current intensity that changes rapidly due to switching in a certain duration. The X-ray imaging system also includes a controlling unit with a random firing switch module (FFW) and exposure control unit (ECU) for operating X-ray sources. The random firing switch module is connected to all X-ray sources. It randomly fires one of the X-ray sources at a time with an externally generated trigger signal. Thus, the activation of each X-ray source and image acquisition occurs simultaneously. When one of the X-ray sources is activated, an associated electronic unit that is connected to a flat panel detector (units in total) will control the electronic trigger signal applied to the flat panel detector so that the acquisition of x-ray imaging data begins simultaneously with the activation of the X-ray source.

FIG. 5 illustrates an exemplary electron beam in an X-ray tube deflection by electric plate pair through a voltage difference. X-ray tube 6 has a focal spot with a finite size at an initial position that changes after an electrical field, or magnetic field has deflected the X-ray tube focal spot to a subsequent position. The multiple X-ray sources are moved at the same speed as the primary motor stage but opposite to that of the primary motor stage on the predetermined track. They are also positioned relative to the first X-ray source and second X-ray source at a selected angle relative to each other. In this example, four pulsed X-ray sources move simultaneously relative to the object at a constant speed as a group and sequentially from one to another as they sweep across the object. A corresponding detector is mounted on the opposite side of the primary motor stage 4 that is parallel to the movement direction of the pulsed X-ray sources.

Electrical deflection plate 7 is located between the X-ray tube cathode and target. Electrical voltage pulses are applied to the electrical deflection plate 7 to control the movement of the focal spot relative to the X-ray source along a tracking axis, as shown in the schematic diagram. The other electrical voltage pulses are applied to the electrical deflection plate 7 to control the movement of the focal spot along a direction perpendicular to the track axis, which results in moving the focal spot back and forth along the track axis in synchronous with other movements on track axis. The magnetic coil is mounted between the X-ray tube cathode and target and is also used to control the movement of the focal spot. By applying different combinations of electrical or magnetic fields simultaneously to deflection device, the X-ray tube electron beam 9 is deflected along the moving direction of primary motor stage 4.

X-ray tube electron beam 9 has its focal spot moved around the x-ray tube stationary axis by an external deflection electrical field (plate) or an external deflection magnetic field (coil). The focal spot constantly moves as the primary motor stage 4 sweeps in a circular path at a predetermined sweep speed to scan an object. This method is done in parallel with multiple X-ray sources.

X-ray tube cathode 10 produces the electron beam 9, and the X-ray is emitted after electron beam 9 hits X-ray tube target 11 and X-ray moving toward the object is referred to as primary X-ray. The deflection coils may be located between the X-ray tube cathode 10 to deflect the electron beam 9 toward the tube target 11 by passing an electrical current through the deflection coils. A high voltage generator (the structure that provides high voltage pulses) connected to the cathode produces an electric pulse and sends it to the deflection coils to deflect the electron beam 9 before it hits the target.

An X-ray tube 6 can include an electron gun, a heated cathode 10, X-ray tube target 11 or other material that generates an electron beam 9 from one end. X-ray tube target 11 is mounted on another end of the X-ray tube 6. The electrical insulator and the material are attached to the housing and conductive with the target. An electrical insulator can be made of many different materials. Examples of electrical insulators can include Teflon and/or other dielectric materials such as glass or mica. Housing can be made of many different materials. Examples of housing can include stainless steel, aluminum, plastic, ceramic, combinations thereof, or any other materials that will not interfere with the transmission of X-rays. Electrical insulators and materials can have the same or different compositions and can be configured in a single or multiple layers between target and housing.

The primary motor stage 4 is mounted on a supporting frame structure 2 that provides housing for the primary motor stage 4. An X-ray flat panel detector 1 to receive X-ray flux is positioned to generate X-ray image projection data from the plurality of X-ray sources. The X-ray sources are arranged on a primary motor stage 4 that moves freely on an arc rail with a predetermined shape. An exposure control unit controls the electrical field applied to each X-ray source to deflect the X-ray tube electron beam 9. An X-ray source moves simultaneously relative to an object on a pre-defined track at a constant speed as a group. Each X-ray source focal spot can also move rapidly around its static position at a small distance by deflection electrical field or deflection magnetic field. When an X-ray tube focal spot on an individual X-ray source has a speed equal to group speed but an opposite moving direction, the respective X-ray source is triggered through an external exposure control unit. Multiple pulsed X-ray sources result in a much-reduced source travel distance for individual X-ray sources.

A primary motor stage 4 is positioned at a pre-defined initial location and sweeps on an arc track at a constant speed by said primary motor. One or more X-ray sources each moved on the primary motor stage 4. The pre-defined initial location can be set to any of various initial locations depending on how one wishes to position a subject on the X-ray imaging machine for X-ray scanning. Various exemplary locations are chest X-ray scan (ventral/dorsal), chest CT scan, etc.

Various modifications and alterations of the invention will become apparent to those skilled in the art without departing from the spirit and scope of the invention, which is defined by the accompanying claims. It should be noted that steps recited in any method claims below do not necessarily need to be performed in the order they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only and not of limitation. The various diagrams may depict an example architectural or other configuration for the invention, which is done to understand the features and functionality that may be included in the invention. The invention is not restricted to the illustrated example architectures or configurations, but the desired features may be implemented using various alternative architectures and configurations. Indeed, it will be apparent to one of skill in the art how alternative functional, logical, or physical partitioning and configurations may be implemented to implement the desired features of the present invention. Also, many different constituent module names other than those depicted herein may be applied to the various partitions. Additionally, with regard to flow diagrams, operational descriptions, and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects, and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open-ended as opposed to limiting. As examples of the previous, the term "including" should be read as meaning "including, without limitation" or the such as; the term "example" is used to provide exemplary instances of the item in the discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given period or to an item available as of a given time. Instead, they should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

A group of items linked with the conjunction "and" should not be read as requiring that every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements, or components of the invention may be described or claimed in the singular, the plural is contemplated to be within the scope thereof unless limitation to the singular is explicitly stated.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in exemplary block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments enables anyone skilled in the art to make or use the present invention. Various modifications to these embodiments will be readily apparent to those skilled in the art. The generic principles defined herein may be applied to other embodiments without departing from the spirit or scope of the invention. Thus, the present invention is not intended to be limited to the embodiments shown herein but is accorded the most comprehensive scope consistent with the principles and novel features disclosed herein.

While there has been shown several and alternate embodiments of the present invention, it is to be understood that certain changes can be made as would be known to one skilled in the art without departing from the underlying scope of the invention as is discussed and set forth above and below. Furthermore, the embodiments described above are only intended to illustrate the principles of the present invention. They are not intended to limit the scope of the invention to the disclosed elements.

What is claimed is:

1. A fast 3D radiography system comprising:
a primary motor stage moving freely on an arc rail;
a primary motor that engages with said primary motor stage and controls a speed of the primary motor stage;
a plurality of X-ray sources each mounted at the primary motor stage;
a supporting frame structure for the primary motor stage; and
an x-ray flat panel detector.

2. The system of claim 1, comprising a pair of electrical deflection plates on each X-ray tube of X-ray source.

3. The system of claim 1, comprising one or a pair of magnetic deflection coil yoke on each of X-ray tube of X-ray source.

4. The system of claim 1, wherein one or more of the x-ray sources is activated using a predetermined scheme.

5. The system of claim 1, wherein an initial spatial position of the primary motor stage is adjustable by software.

6. The system of claim 1, wherein the result of each and accumulated analysis determines the next X-ray source and exposure condition.

7. The system of claim 1, wherein exposure time of X-ray source is adjustable by software.

8. The system of claim 1, wherein the object is at a standstill.

9. The system of claim 1, wherein each X-ray source comprises an X-ray tube focal spot and wherein the X-ray tube focal spot moves a small distance around a static position on X-ray tube target by deflection electrical field or deflection magnetic field.

10. The system of claim 1, wherein each X-ray source comprises an X-ray tube focal spot and when the X-ray tube focal spot on an individual X-ray source has a speed that equals to a group X-ray source speed but an opposite moving direction, the individual X-ray source is triggered through an external exposure control unit, and wherein the X-ray source stays relatively standstill during the X-ray pulse trigger exposure duration.

11. A method of fast 30 radiography comprising:
positioning a primary motor stage driven by a primary motor;
sweeping the primary motor stage at a predetermined constant speed;
deflecting X-ray tube electron beam with a predetermined sequence;
electrically activating an X-ray source when an X-ray tube focal spot moves in the opposite direction to that of the primary motor stage and at a selected speed of the primary motor stage; and
acquiring image data from the X-ray flat panel detector.

12. The method of claim 11, comprising providing a pair of electrical deflection plates on each X-ray tube of X-ray source.

13. The method of claim 11, comprising providing one or a pair of deflection magnetic coil yoke on each of X-ray tube of X-ray source.

14. The method of claim 11, wherein 4D imaging is performed by adding a time component to 3D spatial imaging data.

15. The method of claim 11, comprising changing a sweep angle based on a region of interest.

16. The method of claim 11, wherein X-ray imaging data is acquired and reconstructed in real- time to determine the next X-ray source and exposure condition.

17. The method of claim 11, comprising changing an X-ray source voltage input based on object density during a sweep.

18. The method of claim 11, wherein the x-ray flat panel detector 1 s coupled to a linear stage to adjust a position based on locations of X-ray sources.

19. The method of claim 11, wherein each X-ray source comprises an X-ray tube focal spot and wherein the X-ray tube focal spot moves a small distance around a static position on X-ray tube target by deflection electrical field or deflection magnetic field.

20. The method of claim 11, wherein each X-ray source comprises an X-ray tube focal spot and when the X-ray tube focal spot on an individual X-ray source has a speed that equals to a group X-ray source speed but an opposite moving direction, the individual X-ray source is triggered through an external exposure control unit, and wherein the X-ray source stays relatively standstill during the X-ray pulse trigger exposure duration.

* * * * *